United States Patent
Engler et al.

(10) Patent No.: US 7,373,819 B2
(45) Date of Patent: May 20, 2008

(54) STRESS SENSITIVE HUMIDITY SENSOR BASED ON A MEMS STRUCTURE

(75) Inventors: Kevin J. Engler, Freeport, IL (US); Jamie W. Speldrich, Freeport, IL (US)

(73) Assignee: Honeywell International Inc., Morristown, NJ (US)

( * ) Notice: Subject to any disclaimer, the term of this patent is extended or adjusted under 35 U.S.C. 154(b) by 284 days.

(21) Appl. No.: 11/242,577

(22) Filed: Sep. 30, 2005

(65) Prior Publication Data

US 2007/0074569 A1 Apr. 5, 2007

(51) Int. Cl.
*G01N 27/02* (2006.01)
*G01N 19/00* (2006.01)

(52) U.S. Cl. .............. 73/335.03; 73/335.02; 73/29.01

(58) Field of Classification Search ..................
73/335.02–335.11, 29.01, 29.02, 29.03, 29.04, 73/29.05, 493
See application file for complete search history.

(56) References Cited

U.S. PATENT DOCUMENTS

| | | | | |
|---|---|---|---|---|
| 4,877,329 A | * | 10/1989 | Sauerbaum et al. .......... 374/28 |
| 5,563,341 A | * | 10/1996 | Fenner et al. ............. 73/335.11 |
| 6,016,686 A | * | 1/2000 | Thundat ..................... 73/23.2 |
| 6,073,480 A | * | 6/2000 | Gokhfeld .................... 73/29.02 |
| 6,126,311 A | * | 10/2000 | Schuh ......................... 374/21 |
| 6,483,324 B1 | * | 11/2002 | Mitter et al. ................ 324/689 |
| 6,607,854 B1 | | 8/2003 | Rehg et al. ................... 429/13 |
| 6,777,120 B2 | * | 8/2004 | Nelson et al. ............... 429/22 |
| 6,797,631 B2 | * | 9/2004 | Kim et al. ................... 438/700 |
| 6,866,819 B1 | * | 3/2005 | Chandra et al. ............. 422/50 |
| 6,883,371 B2 | * | 4/2005 | Sugaya et al. .......... 73/335.05 |
| 7,028,531 B2 | * | 4/2006 | Nikolaus ................... 73/29.05 |
| 7,032,448 B2 | * | 4/2006 | Hamamoto .............. 73/335.04 |
| 2002/0040598 A1 | | 4/2002 | Sugaya et al. .......... 73/335.02 |
| 2002/0177017 A1 | | 11/2002 | Nelson et al. ................ 429/22 |
| 2002/0190840 A1 | | 12/2002 | Fujita et al. ................. 338/35 |
| 2003/0054215 A1 | | 3/2003 | Doshi et al. ................. 429/26 |
| 2003/0124401 A1 | | 7/2003 | Issacci et al. ................ 429/26 |
| 2004/0254306 A1 | | 12/2004 | Isogai et al. ................ 525/435 |

* cited by examiner

*Primary Examiner*—Helen C. Kwok
(74) *Attorney, Agent, or Firm*—Kermit D. Lopez; Luis M. Ortiz; William B. Shelby

(57) ABSTRACT

A humidity sensing apparatus and method include a substrate and a MEMS structure, wherein the MEMS structure is supported by the substrate. The MEMS structure comprises a humidity-sensitive material in association with a movable member such that when the humidity-sensitive material changes with humidity, the MEMS structure moves the movable member, thereby providing an indication of humidity based on a stress within the MEMS structure.

20 Claims, 4 Drawing Sheets

STRESS SENSITIVE HUMIDITY SENSOR BASED ON A MEMS STRUCTURE

TECHNICAL FIELD

Embodiments are generally related to sensing devices and methods. Embodiments are also related to humidity sensors. Embodiments are additionally related to micro electromechanical machines (MEMS) devices and components. Embodiments are further related to fuel cells.

BACKGROUND OF THE INVENTION

Humidity sensors are utilized in a variety of commercial, industrial and consumer applications. A humidity sensor converts a change resulting from humidity and moisture to an electric quantity and executes signal processing by use of an electronic circuit. It has been widely employed to satisfy a demand for humidity control in a variety of objects One area where humidity sensing is particularly important is the area of fuel cells, including hydrogen based fuel cell devices. Fuel cells are increasingly being used as a power source in a wide variety of different applications. Fuel cells have also been proposed for use in electrical vehicular power plants to replace internal combustion engines. A solid-polymer-electrolyte fuel cell includes a membrane that is sandwiched between an anode and a cathode. To produce electricity through an electrochemical reaction, hydrogen ($H_2$) is supplied to the anode and air or oxygen ($O_2$) is supplied to the cathode.

In a first half-cell reaction, dissociation of the hydrogen ($H_2$) at the anode generates hydrogen protons (H+) and electrons. The membrane is proton conductive and dielectric. As a result, the protons are transported through the membrane while the electrons flow through an electrical load that is connected across the electrodes. In a second half-cell reaction, oxygen ($O_2$) at the cathode reacts with protons (H+), and electrons are taken up to form water ($H_2O$).

To operate efficiently and to produce a maximum amount of electricity, the fuel cell must be properly humidified. To achieve the proper humidity range, the hydrogen stream and/or the air stream are typically humidified by one of several methods known in the art. Conventional humidity control methods generally fail to sufficiently control the humidity of the hydrogen and air streams to the fuel cell. Providing too much humidity to the fuel cell blocks the reacting gases from accessing the catalyst thereby impeding the electrochemical reaction between the hydrogen and air and reducing the production of electricity. Providing too little humidity to the fuel cell restricts or limits the proton transportation required for reaction within the fuel cell.

In order to provide a humidity sensor, which can be adapted for use in applications such as, but not limited to, fuel cells, an improved sensor structure and methodology is required. The humidity sensor described herein therefore offers such a device.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the present invention to provide for an improved sensing apparatus and method.

It is another aspect of the present invention to provide for an improved humidity sensor.

It is a further aspect of the present invention to provide for an improved humidity sensor, which incorporates MEMS components and features.

The aforementioned aspects and other objectives and advantages can now be achieved as described herein. A humidity sensing apparatus and method are disclosed. In general a substrate and a MEMS structure are provided, wherein the MEMS structure is supported by the substrate. The MEMS structure comprises a humidity-sensitive material in association with a movable member such that when the humidity-sensitive material changes with humidity, the MEMS structure moves the movable member, thereby providing an indication of humidity based on a stress within the MEMS structure.

A base can also be formed upon the substrate, wherein the MEMS structure and the humidity-sensitive material and the movable member thereof are formed on and supported by the base. The base can further function as a locator. The humidity-sensitive material can be, for example, a humidity-sensitive component such as, for example, a perfluorinated polymer or CAB. Additionally, an integrated circuit can be formed upon the MEMS structure. A plurality of electrical leads, which communicate electrically with the integrated circuit, can be further connected to the substrate. The substrate and the MEMS structure can be located within, for example, a fuel cell for the detection of humidity within the fuel cell. The apparatus and method disclosed herein solve the need in fuel cells for environmentally tough materials that are condensation and temperature resistant.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

Figure 1:
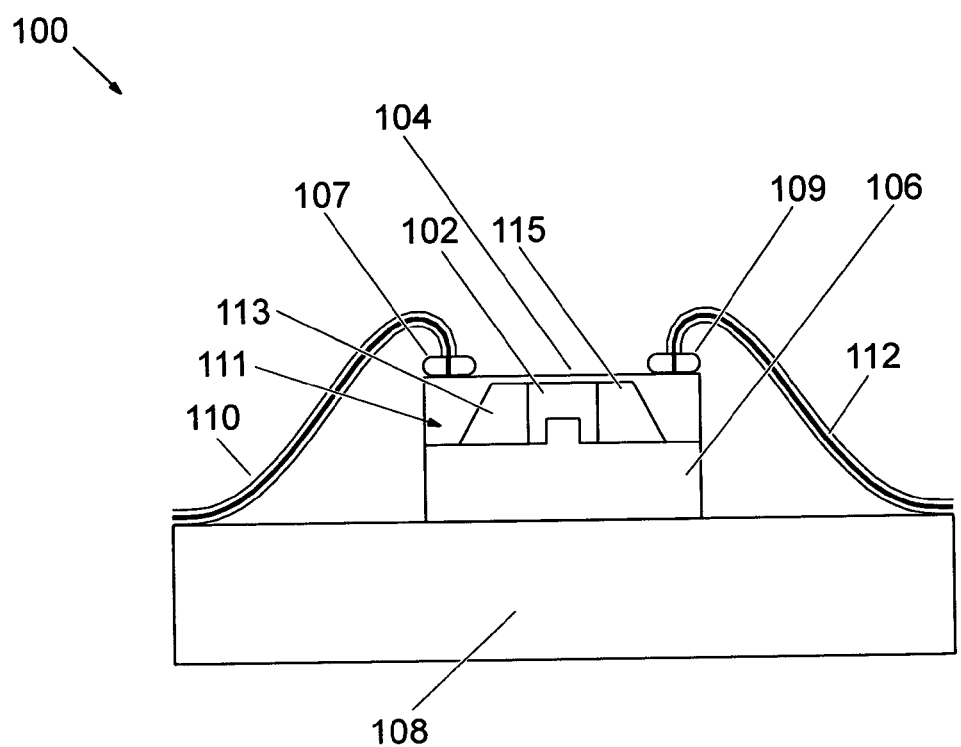
FIG. 1 illustrates a side-view of a stress-sensitive humidity sensor that can be implemented in accordance with a preferred embodiment.

FIG. 1 illustrates a side-view of a stress-sensitive humidity sensing apparatus 100 that can be implemented in accordance with a preferred embodiment. Note that in FIGS. 1-3, identical or similar parts or elements are generally indicated by identical reference numerals. Stress-sensitive humidity sensing apparatus 100 is formed on a substrate 108 and includes a base 106, which can function both as a base component and a locator feature. Stress-sensitive humidity sensing apparatus 100 also includes one or more leads 110 and 112, which respectively incorporate lead connector portions 107 and 109. Additionally, a humidity-sensitive section 102 is also provided, which is maintained by and incorporated into a stress-sensitive MEMS device 104.

Note that as utilized herein, the term "MEMS" refers generally to the term "microelectromechanical systems". MEMS devices generally include micro machined substrates integrated with electronic microcircuits. Such devices may form, for example, micro sensors or micro actuators, which operate based on, for example, electromagnetic, electrostrictive, thermoelectric, piezoelectric, or piezoresistive effects. MEMS devices have been formed on insulators or other substrates using micro-electronic techniques such as photolithography, vapor deposition, and etching. In general, MEMS devices utilize microfabrication methods to develop moving parts linked to electrical components for detection and actuation. A MEMS device can be thought of as a microscopic device that offers both electrical and mechanical functionality, which is manufactured in a batch process. Less formally, the term MEMS can be used to describe batch-fabricated mechanical devices even when there is no electrical functionality or system (i.e. a single mechanical component), or interchangeably with MST or micro machines.

The humidity-sensitive section 102 is preferably formed from a humidity-sensitive material, such as, for example, a perfluorinated polymer. One example of a perfluorinated polymer that can be adapted for use in order to implement humidity-sensitive section 102 is Nafion®, which is a perfluorinated polymer that contains small proportions of sulfonic or carboxylic ionic functional groups. Note that Nafion® is a registered trademark of E. I. Du Pont De Nemours and Company based in Wilmington, Del. Another example of a material that can be utilized to implement humidity-sensitive section 102 is cellulose acetate butyrate (CAB). CAB is generally known as an ester of cellulose, which is created by the action of a mixture of acetic, and butyric acids and their anhydrides on purified cellulose. CAB is often used in the manufacture of plastics that are similar in general properties to cellulose acetate but are tougher and have better moisture resistance and dimensional stability.

The stress-sensitive MEMS device 104 also incorporates a mechanical movable member 111 made of member sections 113 and 115. The stress-sensitive humidity sensing apparatus 100 thus utilizes a humidity-sensitive material such as Nafion or CAB for humidity-sensitive section 102 in association with the mechanical movable member 111 in a MEMS structure or MEMS device 104 that moves the mechanical movable member 111 when the humidity sensitive material or substance changes with humidity. The moving member 111 can then be sensed utilizing piezoelectric components or another appropriate means of sensing movement.

Figure 2:
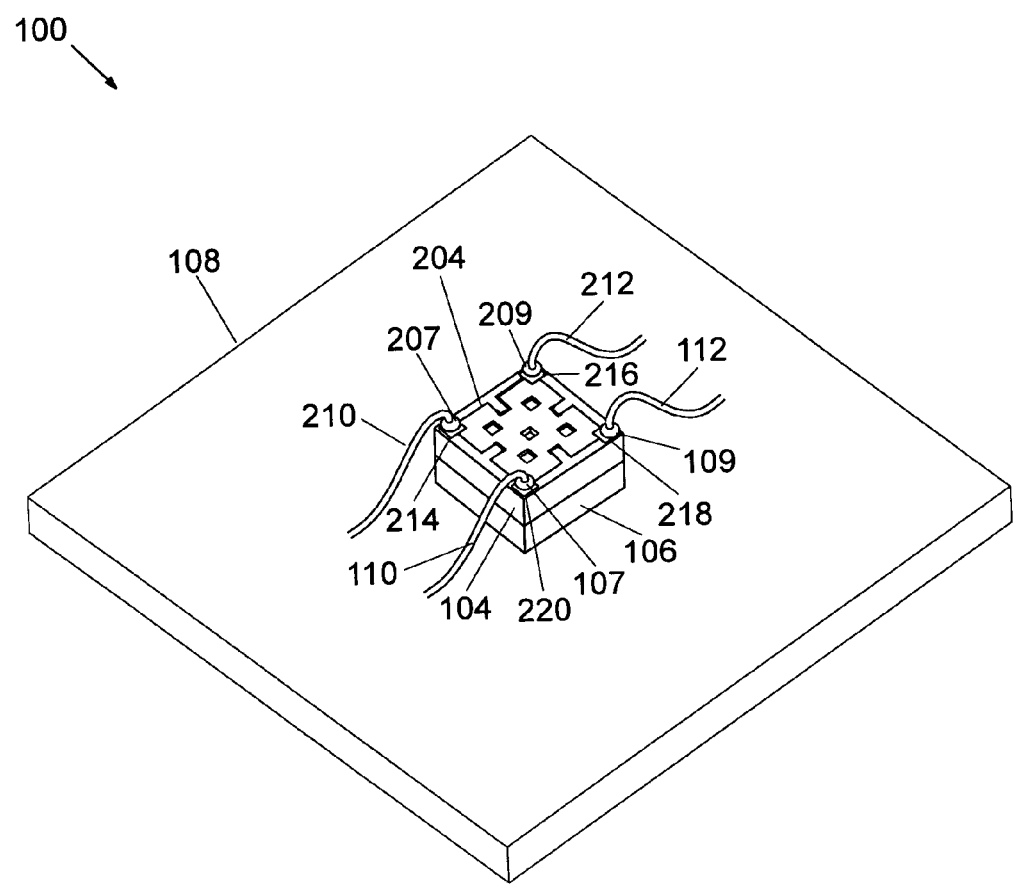
FIG. 2 illustrates a perspective view of the stress-sensitive humidity sensor depicted in FIG. 1, which can be implemented in accordance with a preferred embodiment.

FIG. 2 illustrates a perspective view of the stress-sensitive humidity sensing apparatus 100 depicted in FIG. 1, in accordance with a preferred embodiment. As indicated by the perspective of stress-sensitive humidity sensing apparatus 100 illustrated in FIG. 2, an electrical integrated circuit line 204 can be formed atop the stress-sensitive MEMS device 104. Two other electrical leads 210 and 212 are also depicted in the perspective view depicted in FIG. 2. Leads 210 and 212 are respectively connected to lead connector portions 207 and 209, which are similar to the lead connector portions 107 and 109, which are also depicted in FIG. 2. Note that each lead connector portion 107, 109 and 207, 209 is respectively connected to associated electrical connection pads 220, 218 and 214, 216. Note that such pads 220, 218 and 214, 216, form a part of the electrical integrated circuit line 204. The locator portion or base 106 is also depicted in FIG. 2 as located above substrate 108.

Figure 3:
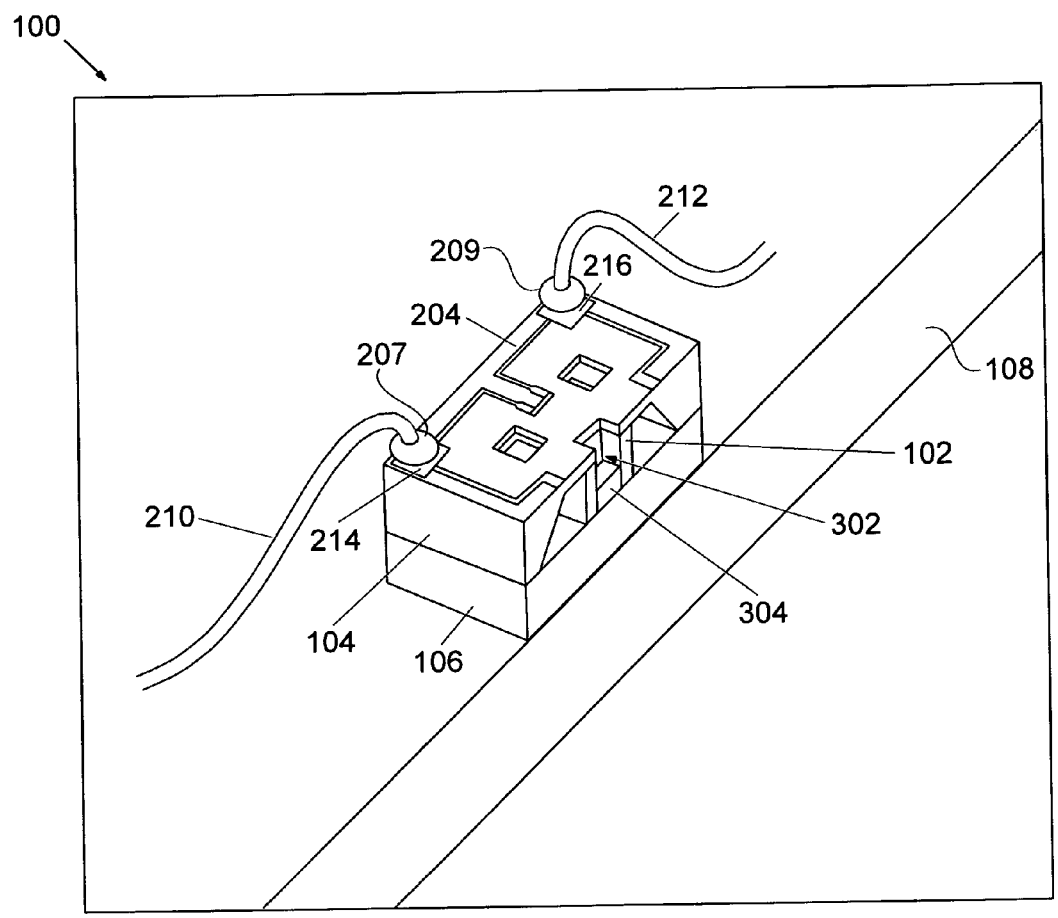
FIG. 3 illustrates a partial perspective view of the stress-sensitive humidity sensor depicted in FIGS. 1-2 in accordance with a preferred embodiment.

FIG. 3 illustrates a partial perspective view of the stress-sensitive humidity sensing apparatus 100 depicted in FIGS. 1-2 in accordance with a preferred embodiment. Stress-sensitive humidity sensing apparatus 100 depicted in FIG. 3 generally includes the same components depicted in FIG. 102, but from a partial sectional perspective. For example, leads 210 and 212 are depicted in FIG. 3 in association with lead connector portions 207 and 209 and respective electrical connection pads 214, 216. Also depicted in FIG. 3 is the humidity-sensitive section 102, which is maintained by and incorporated into the stress-sensitive MEMS device 104. Note that the stress-sensitive MEMS device 104 is shaped with a gap or indentation 302 that is located directly above a protruding portion 304 of base 106. The protruding portion 304 forms a part of base 106.

Figure 4:
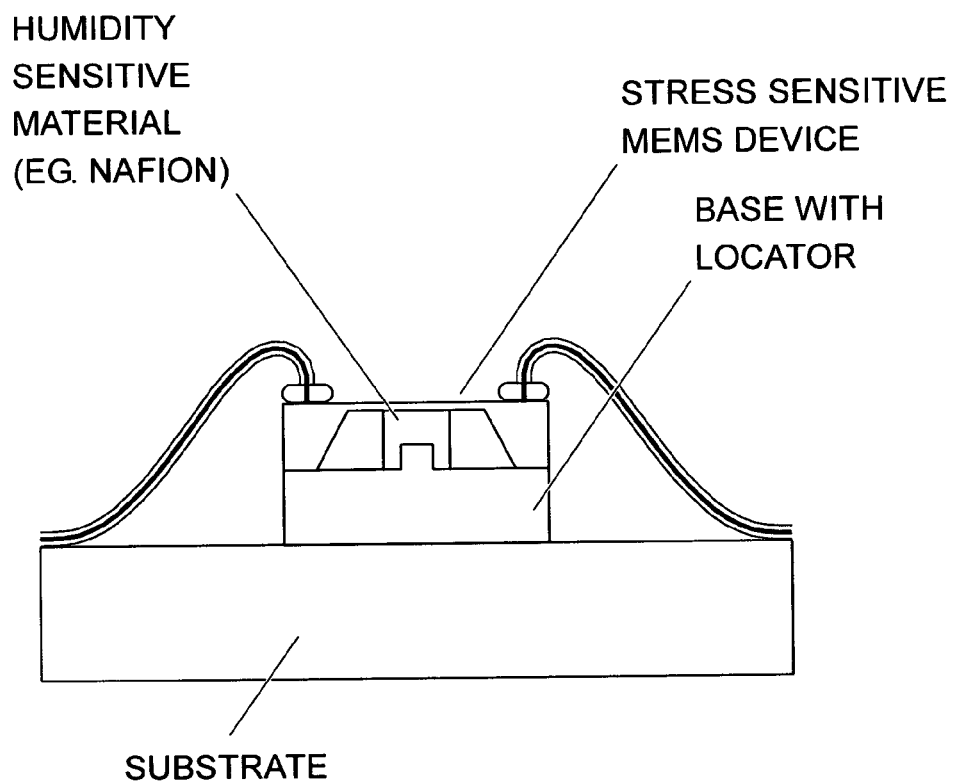
FIG. 4 illustrates a side-view of a stress-sensitive humidity sensor that can be implemented in accordance with a preferred embodiment.

FIG. 4 illustrates a side-view of a stress-sensitive humidity sensing apparatus that can be implemented in accordance with a preferred embodiment. Stress-sensitive humidity sensing apparatus is formed on a substrate and includes a base, which can function both as a base component and a locator feature. Additionally, a humidity-sensitive material is also provided, which is maintained by and incorporated into a stress-sensitive MEMS device.

The humidity sensor apparatus described herein can be used, for example, for measuring the moisture content of air; the moisture content of exhaust gas of an internal combustion engine of, for example, an automobile, ship, or airplane, particularly the moisture content of an atmosphere containing substantially no oxygen and containing a reducing gas; or the moisture content of a highly reducing atmosphere surrounding a fuel electrode or an air electrode of a fuel cell.

One example of a fuel cell system to which the humidity sensing apparatus 100 can be adapted therewith is disclosed in U.S. Patent Publication No. 20030054215, entitled "Compact integrated solid oxide fuel cell system," which published on Mar. 20, 2003 to Rajiv Doshi, et al. U.S. Patent Publication No. 20030054215, which is incorporated herein by reference in its entirety and is assigned to Honeywell International Inc., generally describes a compact integrated solid oxide fuel cell power system that includes a fuel cell stack, two stages of heat exchange, and a thermal enclosure.

The system includes a recuperator which exchanges heat between exhaust gas, heated by oxidizing unspent gases from the fuel cell stack in a combustion chamber, and incoming oxidant to pre-heat the oxidant. The solid oxide fuel cell stack has an internal manifold which exchanges heat between incoming fuel and the preheated oxidant. System components are enclosed by thermal insulation. The system can also include a catalytic partial oxidation reformer to pre-heat the fuel during start up. The system can also include an air compressor, fuel storage tank, and pressure relief valve, providing a portable power system.

Another example of a of a fuel cell system to which the humidity sensing apparatus 100 can be adapted therewith is disclosed in U.S. Patent Publication No. 20030124401, entitled "Integrated recuperation loop in fuel cell stack," which published on Jul. 3, 2003 to Farrokh Issacci, Farrokh, et al. U.S. Patent Publication No. 20030124401, which is incorporated herein by reference in its entirety and is assigned to Honeywell International Inc., generally describes a method and apparatus that increase fuel cell reliability and maintainability. The apparatus includes a recuperating loop consisting of a spiral tube that surrounds a stack or a combination of several stacks. If the fuel cell stacks are externally manifolded, the recuperating loop may also surround the external manifold. The spent hot gases from the stack directly flow over the recuperating loop to transfer heat to a coolant flowing through the loop providing heat exchange by convection and radiation. The spent hot gases may be manifolded and may not flow over the recuperating loop. In this case, the heat exchange is by radiation between the hot fuel cell stack(s) and the recuperating loop.

A further example of a fuel cell system to which the humidity sensing apparatus 100 can be adapted therewith is the PEM fuel cell system disclosed in U.S. Pat. No. 6,607,854, entitled "Three-wheel air turbocompressor for PEM fuel cell systems," which issued to Rehg, et al. on Aug. 19, 2003. U.S. Pat. No. 6,607,854, which is incorporated herein by reference in its entirety and which is assigned to Honeywell International Inc. generally describes a fuel cell system comprises a compressor, a fuel processor downstream of the compressor; a fuel cell stack in communication with the fuel processor and compressor; a combustor downstream of the fuel cell stack; a first turbine downstream of the fuel processor; a second turbine downstream of the fuel processor and in parallel flow communication with the first turbine, and the second turbine being mechanically engaged to the compressor and first turbine; a bypass valve intermediate the compressor and second turbine, with the bypass valve enabling a compressed gas from the compressor to bypass the fuel processor; and a distribution valve in communication with the first and second turbines.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A humidity sensing apparatus, comprising:
   a substrate; and
   a MEMS structure supported by said substrate, wherein said MEMS structure comprises a humidity-sensitive material in association with a mechanical movable member such that when said humidity-sensitive material changes with humidity, said MEMS structure moves said mechanical movable member, thereby providing an indication of humidity based on a stress within said MEMS structure.

2. The apparatus of claim 1 further comprising a base formed upon said substrate, wherein said MEMS structure and said humidity-sensitive material and said mechanical movable member thereof are formed on and supported by said base and wherein said mechanical movable member is a non-cantilevered member.

3. The apparatus of claim 2 wherein said base comprises a locator and wherein a protruding portion forms a portion of said base below a gap in said MEMS structure.

4. The apparatus of claim 1 wherein said humidity-sensitive material comprises a perfluorinated polymer.

5. The apparatus of claim 1 wherein said humidity-sensitive material comprises a cellulose acetate butyrate.

6. The apparatus of claim 1 further comprising an integrated circuit formed upon said MEMS structure.

7. The apparatus of claim 6 further comprising a plurality of electrical leads, which communicate electrically with said integrated circuit and are further connected to said substrate.

8. The apparatus of claim 1 wherein said substrate and said MEMS structure are located within a fuel cell for the detection of humidity within said fuel cell.

9. A humidity sensing apparatus, comprising:
   a substrate;
   a base formed upon said substrate;
   a MEMS structure supported by said substrate, wherein said MEMS structure comprises a humidity-sensitive material in association with a mechanical movable member such that when said humidity-sensitive material changes with humidity, said MEMS structure moves said mechanical movable member, thereby providing an indication of humidity based on a stress within said MEMS structure, and wherein said MEMS structure and said humidity-sensitive material and said mechanical movable member thereof are formed on and supported by said base.

10. The apparatus of claim 9 wherein said humidity-sensitive material comprises at least one of the following: a perfluorinated polymer or a cellulose acetate butyrate.

11. A humidity sensing method, comprising:
   providing a substrate; and
   configuring a MEMS structure supported by said substrate, wherein said MEMS structure comprises a humidity-sensitive material in association with a mechanical movable member such that when said humidity-sensitive material changes with humidity, said MEMS structure moves said mechanical movable member, thereby providing an indication of humidity based on a stress within said MEMS structure.

12. The method of claim 11 further comprising:
   forming a base upon said substrate;
   configuring said MEMS structure and said humidity-sensitive material and said mechanical movable member upon said base, wherein said MEMS structure and said humidity-sensitive material and said mechanical movable member are supported by said base.

13. The method of claim 12 wherein said base comprises a locator.

14. The method of claim 11 wherein said humidity-sensitive material comprises a perfluorinated polymer.

15. The method of claim 11 wherein said humidity-sensitive material comprises cellulose acetate butyrate.

16. The method of claim 11 further comprising forming an integrated circuit upon said MEMS structure.

17. The method of claim 16 further comprising providing a plurality of electrical leads, which communicate electrically with said integrated circuit and are further connected to said substrate.

18. The method of claim 17 further comprising locating said substrate and said MEMS structure within a fuel cell for the detection of humidity within said fuel cell.

19. The method of claim 18 wherein said fuel cell comprises a PEM fuel cell.

20. The method of claim 11 wherein said humidity-sensitive material comprises a humidity-sensitive section which is maintained by and incorporated into a stress-sensitive MEMS device formed from said MEMS structure.

* * * * *